US00PP30110P2

(12) United States Plant Patent
Larsen

(10) Patent No.: US PP30,110 P2
(45) Date of Patent: Jan. 15, 2019

(54) ***OSTEOSPERMUM* PLANT NAMED 'SUNOST1701'**

(50) Latin Name: *Osteospermum ecklonis*
Varietal Denomination: SUNOST1701

(71) Applicant: Bjarne Nyholm Larsen, Odense N. (DK)

(72) Inventor: Bjarne Nyholm Larsen, Odense N. (DK)

(73) Assignee: Sunny Gronnegyden APS, Odense N. (DK)

( * ) Notice: Subject to any disclaimer, the term of this patent is extended or adjusted under 35 U.S.C. 154(b) by 0 days.

(21) Appl. No.: 15/731,770

(22) Filed: Jul. 31, 2017

(51) Int. Cl.
*A01H 5/02* (2018.01)

(52) U.S. Cl.
USPC ..... Plt./360

(58) Field of Classification Search
USPC ..... Plt./360
CPC ..... A01H 5/02; A01H 6/148
See application file for complete search history.

*Primary Examiner* — Keith O. Robinson
(74) *Attorney, Agent, or Firm* — C. A. Whealy

(57) ABSTRACT

A new and distinct cultivar of *Osteospermum* plant named 'SUNOST1701', characterized by its upright to outwardly spreading and mounding plant habit; moderately vigorous growth rate; freely branching growth habit; undulating dark green-colored leaves; moderately freely flowering habit; large daisy-type inflorescences with dark yellow-colored ray florets; and good garden performance.

2 Drawing Sheets

Botanical designation: *Osteospermum ecklonis.*
Cultivar denomination: 'SUNOST1701'.

BACKGROUND OF THE INVENTION

The present invention relates to a new and distinct cultivar of *Osteospermum* plant, botanically known as *Osteospermum ecklonis* and hereinafter referred to by the name 'SUNOST1701'.

The new *Osteospermum* plant is a product of a planned breeding program conducted by the Inventor in Odense, Denmark. The objective of the program is to create and develop new *Osteospermum* plants with compact and uniformly mounded plant habit, freely flowering habit and attractive ray and disc floret coloration.

The new *Osteospermum* plant originated from a cross-pollination by the Inventor in May, 2013 of *Osteospermum ecklonis* 'SUNOST1101', disclosed in U.S. Plant Pat. No. 24,162, as the female, or seed, parent with a proprietary selection of *Osteospermum ecklonis* identified as code number 11.30.004, not patented, as the male, or pollen, parent. The new *Osteospermum* plant was discovered and selected by the Inventor as a single flowering plant within the progeny of the stated cross-pollination in a controlled greenhouse environment in Odense, Denmark in May, 2016.

Asexual reproduction of the new *Osteospermum* plant by terminal cuttings in a controlled greenhouse environment in Odense, Denmark since November, 2016 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'SUNOST1701'. These characteristics in combination distinguish 'SUNOST1701' as a new and distinct *Osteospermum* plant:

1. Upright to outwardly spreading and mounding plant habit.
2. Moderately vigorous growth rate.
3. Freely branching growth habit.
4. Undulating dark green-colored leaves.
5. Moderately freely flowering habit.
6. Large daisy-type inflorescences with dark yellow-colored ray florets.
7. Good garden performance.

Plants of the new *Osteospermum* differ primarily from plants of the female parent, 'SUNOST1101', in the following characteristics:

1. Fully expanded leaves of plants of the new *Osteospermum* are longer than fully expanded leaves of plants of 'SUNOST1101'.
2. Inflorescences of plants of the new *Osteospermum* are larger than inflorescences of plants of 'SUNOST1101'.
3. Plants of the new *Osteospermum* and 'SUNOST1101' differ in ray floret color as plants of 'SUNOST1101' have purple-colored ray florets.

Plants of the new *Osteospermum* differ primarily from plants of the male parent selection in the following characteristics:

1. Plants of the new *Osteospermum* and the male parent selection differ in ray floret color as plants of the male parent selection have light yellow-colored ray florets.
2. Plants of the new *Osteospermum* and the male parent selection differ in disc floret color as plants of the male parent selection have light blue-colored disc florets.

Plants of the new *Osteospermum* can be compared to plants of the *Osteospermum ecklonis* 'Sunny Amanda', disclosed in U.S. Plant Pat. No. 16,522. In side-by-side comparisons, plants of the new *Osteospermum* differ from plants of 'Sunny Amanda' in the following characteristics:

1. Plants of the new *Osteospermum* are more compact and not as open as plants of 'Sunny Amanda'.
2. Plants of the new *Osteospermum* have larger leaves than plants of 'Sunny Amanda'.
3. Plants of the new *Osteospermum* and 'Sunny Amanda' differ in ray floret color as plants of 'Sunny Amanda' have light yellow-colored ray florets.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph on the first sheet comprises a side perspective view of a typical flowering plant of 'SUNOST1701' grown in a container.

The photograph on the second sheet is a close-up view of a typical inflorescence of 'SUNOST1701'.

DETAILED BOTANICAL DESCRIPTION

The aforementioned photographs, following observations and measurements describe plants grown during the winter in 11-cm containers in a glass-covered greenhouse in Odense, Denmark and under cultural practices typical of commercial *Osteospermum* production. During the production of the plants, day temperatures ranged from 14° C. to 20° C. and night temperatures averaged 14° C. Plants were pinched one time and were 14 weeks old when the photographs and description were taken. In the following description, color references are made to The Royal Horticultural Society Colour Chart, 2015 Edition, except where general terms of ordinary dictionary significance are used.

Botanical classification: *Osteospermum ecklonis* 'SUNOST1701'.

Parentage:

*Female, or seed, parent.*—*Osteospermum ecklonis* 'SUNOST1101', disclosed in U.S. Plant Pat. No. 24,162.

*Male, or pollen, parent.*—Proprietary selection of *Osteospermum ecklonis* identified as code number 11.30.004, not patented.

Propagation:

*Type.*—Terminal vegetative cuttings.

*Time to initiate roots, summer.*—About twelve days at temperatures about 18° C.

*Time to initiate roots, winter.*—About 14 days at temperatures about 18° C. to 20° C.

*Time to produce a rooted cutting, summer.*—About 20 days at temperatures about 18° C. to 20° C.

*Time to produce a rooted cutting, winter.*—About 28 days at temperatures about 18° C.

*Root description.*—Medium in thickness, fibrous; typically whitish in color, actual color of the roots is dependent on substrate composition, water quality, fertilizers, substrate temperature and physiological age of roots.

*Rooting habit.*—Freely branching; medium density.

Plant description:

*Plant and growth habit.*—Upright to outwardly spreading and mounding plant habit; inflorescences positioned above and beyond the foliar plane on moderately strong peduncles; moderately vigorous growth habit; moderate growth rate.

*Plant height, soil level to top of foliar plane.*—About 21.1 cm.

*Plant height, soil level to top of floral plane.*—About 23.5 cm.

*Plant diameter.*—About 29.4 cm.

*Lateral branches.*—Quantity per plant: Freely branching habit with about six primary branches developing per plant, primary branches each with about two secondary branches; pinching enhances branching potential. Length: About 8.2 cm. Diameter: About 4 mm. Internode length: About 3 mm. Strength: Moderately strong. Aspect: Primary branches, about 20° to 60° from vertical; secondary branches about 30° from primary branch axis. Texture and luster: Smooth, glabrous; glossy. Color, developing: Close to 144A. Color, fully developed: Close to 143C.

*Leaf description.*—Arrangement: Alternate, simple; sessile. Length: About 8.2 cm. Width: About 3.7 cm. Shape: Runcinate; undulate. Apex: Obtuse to bluntly acute. Base: Long attenuate. Margin: Shallow and divergent lobes. Texture and luster, upper surface: Smooth, glabrous except along margins, moderately pubescent; moderately glossy. Texture and luster, lower surface: Smooth, glabrous except along margins, moderately pubescent; slightly glossy. Venation pattern: Pinnate, arcuate. Color: Developing leaves, upper surface: Close to between 137A and 141A. Developing leaves, lower surface: Close to 143A to 143B. Fully expanded leaves, upper surface: Close to darker than NN137A; venation, close to 143A. Fully expanded leaves, lower surface: Close to 137B to 137C; venation, close to 144B.

Inflorescence description:

*Appearance.*—Daisy-type inflorescence form with oblanceolate-shaped ray florets; inflorescences terminal and axillary and positioned above and beyond the foliar plane on moderately strong peduncles; disc and ray florets developing acropetally on a capitulum; inflorescences face mostly upright.

*Flowering habit.*—Moderately freely flowering habit with about 36 inflorescences developing per plant.

*Fragrance.*—None detected.

*Flowering response.*—In Denmark, plants of the new *Osteospermum* flower continuously from autumn into the winter; plants begin flowering about ten to twelve weeks after pinching.

*Inflorescence longevity.*—Inflorescences of plants of the new *Osteospermum* last about ten days on the plant; inflorescences persistent.

*Inflorescence buds.*—Height: About 2 cm. Diameter: About 1.6 cm. Shape: Broadly ovate. Texture and luster: Immature ray florets, smooth and glabrous; involucral bracts, moderately pubescent; matte. Color: Immature ray florets, close to between 154B and 1A; involucral bracts, close to 138A.

*Inflorescence size.*—Diameter: Large, about 9 cm. Depth (height): About 2 cm. Disc diameter: About 1.9 cm.

*Receptacles*.—Diameter: About 3 mm. Height: About 3 mm. Shape: Rhomboidal. Color: Close to 145D.

*Ray florets*.—Quantity per inflorescence and arrangement: About 24 ray florets arranged in about two whorls. Length: About 4.3 cm. Width: About 1 cm. Shape: Oblanceolate. Apex: Shallowly praemorse. Base: Attenuate. Margin: Entire. Aspect: Slightly upright; reflexing with development. Texture and luster, upper surface: Smooth, glabrous; velvety; matte. Texture and luster, lower surface: Smooth, glabrous; moderately velvety; slightly glossy. Color: When opening, upper surface: Close to 9A. When opening, lower surface: Close to 6A to 6B. Fully opened, upper surface: Close to between 9A and 12A; venation, similar to lamina color; with development, color becoming closer to 12A and fading to close to 9B towards the base. Fully opened, lower surface: Close to 7A; center, tinged with close to 194B; venation, close to 143C; with development, color becoming closer to between 12A and 13A, fading to close to 12B towards the base and center, tinged with close to 197B.

*Disc florets*.—Quantity per inflorescence and arrangement: About 80 disc florets spirally arranged in about five whorls at the center of the receptacle. Length: About 9 mm. Diameter, apex: About 4 mm. Diameter, base: About 1 mm. Shape: Tubular; apex dentate, five-pointed. Texture and luster, inner and outer surfaces: Smooth, glabrous; glossy. Color, immature, inner and outer surfaces: Apex: Close to N200B. Mid-section: Close to N187A. Base: Close to NN155B. Color, mature, inner and outer surfaces: Apex: Close to 199B. Mid-section: Close to N77B. Base: Close to NN155B.

*Phyllaries*.—Quantity per inflorescence and arrangement: About 20 phyllaries arranged in about two whorls. Length: About 1.2 cm. Width: About 2 mm. Shape: Lanceolate. Apex: Narrowly acute. Base: Cuneate. Margin: Entire. Texture and luster, upper surface: Smooth, glabrous; moderately glossy. Texture and luster, lower surface: Moderately pubescent; matte. Color, upper surface: Close to 146B. Color, lower surface: Close to 137D.

*Peduncles*.—Length, terminal peduncle: About 8.7 cm. Diameter, terminal peduncle: About 2.5 mm. Length, third peduncle: About 10.7 cm. Diameter, third peduncle: About 2.5 mm. Strength: Moderately strong. Aspect, terminal peduncle: Mostly upright. Aspect, third peduncle: About 30° from lateral branch axis. Texture and luster: Moderately pubescent; moderately glossy. Color: Close to 138B.

*Reproductive organs*.—Androecium: Present on disc florets only. Quantity per floret: About five. Filament length: About 3 mm. Filament color: Close to NN155B. Anther shape: Narrowly oblong. Anther length: About 3 mm. Anther color: Close to darker than 200A. Pollen amount: Moderate to abundant. Pollen color: Close to 23A. Gynoecium: Present on disc florets only. Pistil length: About 6 mm. Stigma diameter: About 3 mm. Stigma shape: Cleft. Stigma color: Close to between 200A and 203A. Style length: About 3 mm. Style color: Close to NN155B. Ovary color: Close to 157C to 157D.

*Seeds and fruits*.—Seed and fruit development has not been observed on plants of the new *Osteospermum* to date.

Disease & pest resistance: Plants of the new *Osteospermum* have not been shown to be resistant to pathogens and pests common to *Osteospermum* plants.

Garden performance: Plants of the new *Osteospermum* have been observed to have good garden performance and to tolerate rain, wind, high temperatures about 40° C. and to be suitable for USDA Hardiness Zones 9 to 11.

It is claimed:

1. A new and distinct *Osteospermum* plant named 'SUNOST1701' as illustrated and described.

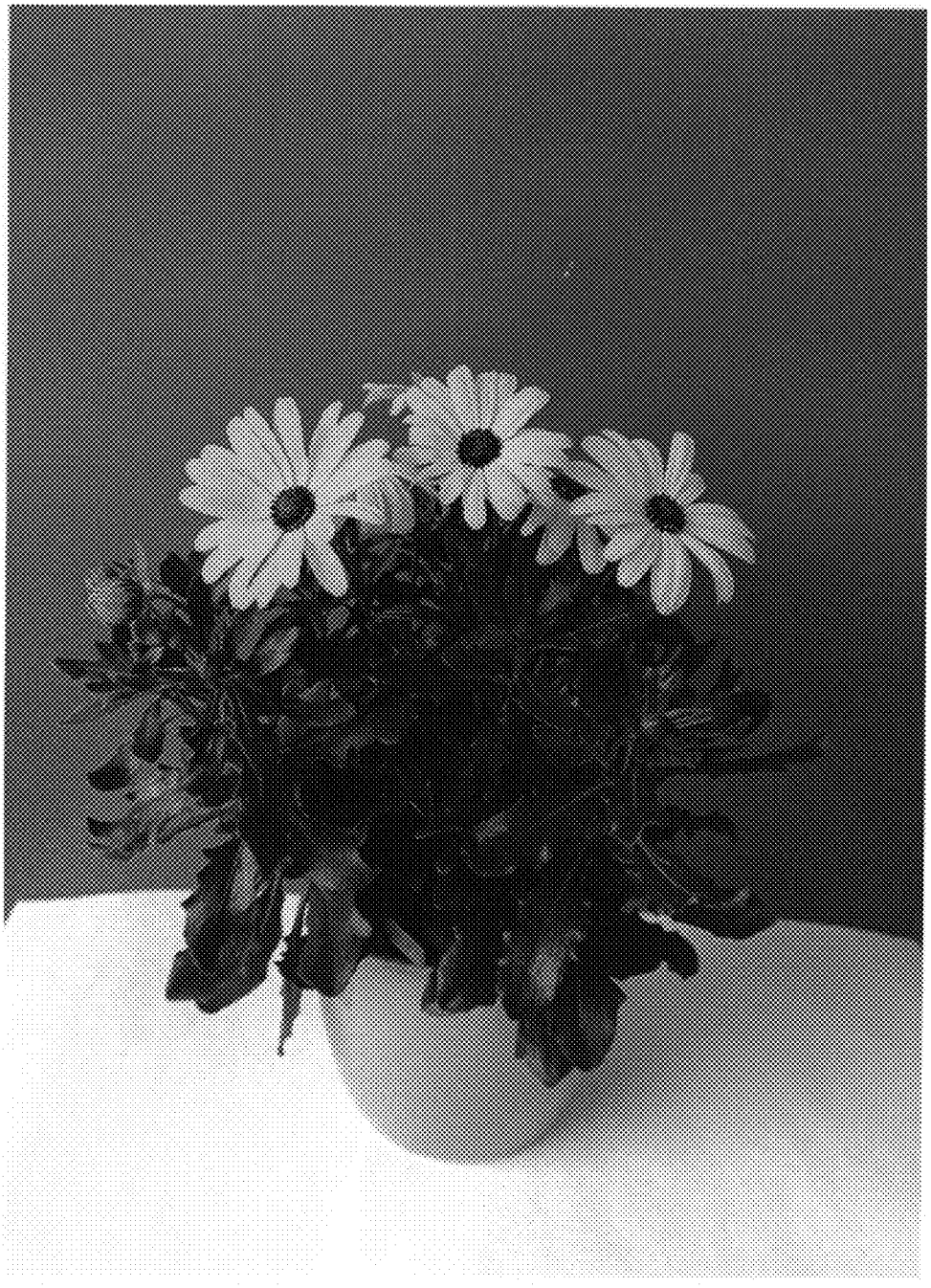

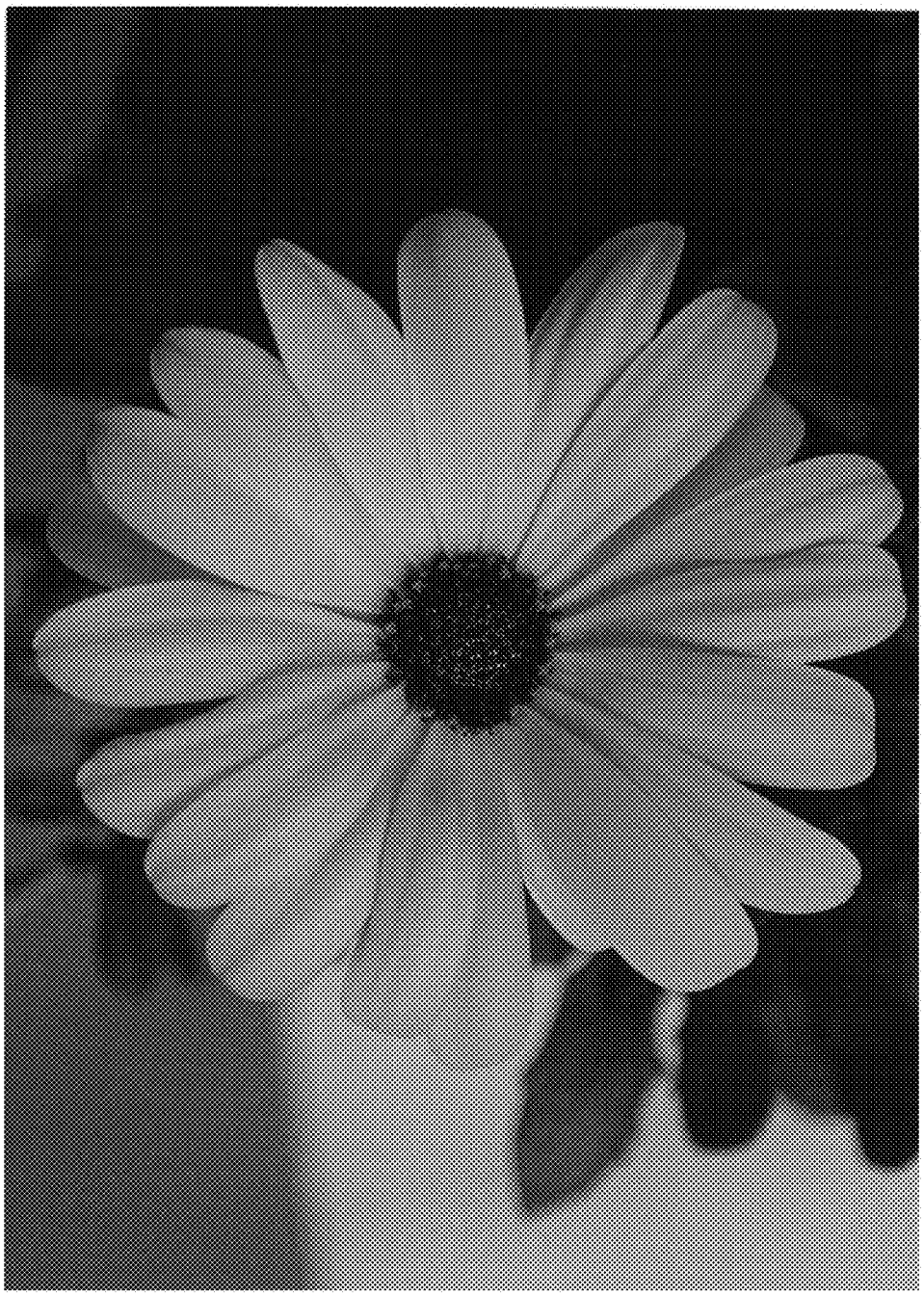

* * * * *